United States Patent [19]

Ford et al.

[11] Patent Number: 5,200,090

[45] Date of Patent: Apr. 6, 1993

[54] MULTIPLE FLUID SOURCE ISOLATION, METERING AND ALARM SYSTEM AND METHOD

[75] Inventors: Michael G. Ford, Orange; Paul R. Prince, San Juan Capistrano, both of Calif.

[73] Assignee: Baxter International Inc., Deerfield, Ill.

[21] Appl. No.: 769,335

[22] Filed: Oct. 1, 1991

Related U.S. Application Data

[63] Continuation of Ser. No. 502,395, Mar. 30, 1990, abandoned.

[51] Int. Cl.$^5$ .................... B01D 35/157; B01D 21/30; B01D 61/32
[52] U.S. Cl. ....................... 210/739; 73/861; 210/85; 210/86; 210/87; 210/88; 210/94; 210/96.2; 210/104; 210/135; 210/137; 210/143; 210/188; 210/195.2; 210/639; 210/645; 210/646; 210/647; 210/744; 210/929; 604/6
[58] Field of Search ............... 210/85, 86, 87, 88, 210/94, 96.2, 104, 135, 137, 143, 188, 195.2, 639, 645, 646, 647, 929, 739, 744; 604/6; 73/861

[56] References Cited

U.S. PATENT DOCUMENTS

| | | | |
|---|---|---|---|
| 4,096,859 | 6/1978 | Agarwal et al. | 210/929 |
| 4,144,943 | 3/1979 | Gallo | 177/50 |
| 4,204,957 | 5/1980 | Weickhardt | 210/929 |
| 4,240,408 | 12/1980 | Schael | 210/929 |
| 4,354,116 | 10/1982 | Tsukamoto | 250/576 |
| 4,447,191 | 5/1984 | Bilstad et al. | 604/6 |
| 4,458,539 | 7/1984 | Bilstad et al. | 604/6 |
| 4,655,742 | 4/1987 | Vantard | 604/6 |

FOREIGN PATENT DOCUMENTS

| | | |
|---|---|---|
| 0243284 | 10/1987 | European Pat. Off. . |
| 0329786 | 8/1989 | European Pat. Off. . |
| 3637771 | 12/1987 | Fed. Rep. of Germany . |
| 3739240 | 5/1988 | Fed. Rep. of Germany . |
| 3737304 | 5/1989 | Fed. Rep. of Germany . |
| 2397197 | 11/1978 | France . |
| 2606639 | 11/1987 | France . |
| WO87/01025 | 2/1987 | PCT Int'l Appl. . |
| 550594 | 12/1985 | Spain . |

OTHER PUBLICATIONS

"A High-precision Control System for Sterile Pulsation-damped Metering for Biomedical Engineering Purposes", H. Merz, M. Pandit, Chr. Oldendorf, *Biomedizinische Technik*, vol. 35, No. 1/2, Jan./Feb. 1990, pp. 5-9.

*Primary Examiner*—Robert A. Dawson
*Assistant Examiner*—Sun Uk Kim
*Attorney, Agent, or Firm*—Bruce M. Canter; June M. Bostich

[57] ABSTRACT

A system is provided for weighing and monitoring flow from multiple fluid sources into a flow system wherein incoming fluid is received in a weighing bag attached to a control system for monitoring the amount of fluid passed through the weighing bag and for preventing admission of air into the flow system. An alarm attached to the weighing bag warns when fluid in the weighing bag is approaching empty, so that the fluid in the weighing bag can be replenished from the fluid source before the weighing bag runs dry. If fluid in the weighing bag is not replenished, the system automatically shuts down.

The fluid pump can be absolutely calibrated using the controlled admission of known amounts of fluid into the weighing bag so that the amount of fluid introduced into the flow system through the weighing bag can be calculated automatically.

53 Claims, 3 Drawing Sheets

MULTIPLE FLUID SOURCE ISOLATION, METERING AND ALARM SYSTEM AND METHOD

This is a continuation of application Ser. No. 07/502,395 filed on Mar. 30, 1990, now abandoned.

BACKGROUND OF THE INVENTION

1. Field of the Invention

This invention relates to a fluid flow system for metering and monitoring flow from multiple liquid sources and more particularly to a plasmapheresis blood flow control system which meters and monitors liquid flow from several sources isolated from handling noise and gives advanced warning when fluid sources are depleted.

2. Discussion of the Prior Art

In fluid flow systems the need arises for controlling sequential or simultaneous influx from multiple fluid sources, especially those of limited capacity. In some cases it is desirable to monitor the total influx from such fluid sources so as to match the amount of fluid withdrawn from the system at another point or in another operation. For instance, plasmapheresis systems are known which require the withdrawal from and subsequent reinfusion of bodily fluids to a living subject in known or fixed amounts. The subject is usually a human or animal, but might also be a cadaver.

In the case of a plasmapheresis system, whole blood is extracted from the subject, plasma is separated from the whole blood, and an extraction product containing a higher concentration of blood cells than the whole blood is reinfused into the subject while the separated plasma is retained and used for desired purposes, treated to alleviate an undesirable condition, or discarded as unfit for further use. To compensate for plasma removed from the patient, a selected volume of replacement fluid is infused into the patient to replace the volume of plasma separated from the whole blood. The use of replacement fluids often has a therapeutic aim. Many undesirable components of blood, including diseased cells, antigens, and the like, are held in suspension therein. During therapeutic plasma exchange, these undesirable components are separated from the blood and removed with the plasma fraction, leaving the blood cleansed and healthier. The replacement fluids used during therapeutic plasma exchange can comprise a variety of fluids, such as saline, thawed plasma, and various therapeutic fluids, depending upon the desires of the treating physician. In such a case it is often desirable to control the amount and rate of each of the replacement fluids administered to the patient.

Determining the exact amount of any given replacement fluid administered to the patient during therapeutic plasma exchange is complicated by the use in modern plasmapheresis machines of disposable plastic tubing harness sets. Although manufactured to specifications as exact as possible, the flow characteristics of each plastic harness set differ somewhat from those of all others.

Therefore, despite all efforts to calibrate the peristaltic pumps with which the harness sets are used to provide sterile, non-invasive therapy, the pumps deliver at slightly different rates dependent upon the individual flow characteristics of the harness set used. The need exists, therefore, for a method of monitoring and controlling with increased precision the amount of each replacement fluid used during therapy.

Yet another problem inherent in monitoring the weight of process fluids comes from inaccuracies introduced due to motion of the fluids being monitored. For instance, the motion of replacement fluids flowing from a weighing bag is sufficient to affect the accuracy of delicate balances used in weighing by mechanical means. The need exists, therefore, for a way to isolate the fluids weighed from the effects of mass transport.

To optimize use of processing equipment and support personnel while minimizing inconvenience and discomfort to the patient, it is also desirable to reinfuse bodily fluids as rapidly and safely as possible. However, replacement fluids, usually saline, are commonly prepackaged in sterile containers of predetermined volume, necessitating that more than one container of replacement fluid be infused into the patient to replace the plasma removed during a typical session of plasmapheresis. If the containers of saline are fed sequentially into the replacement line for reinfusion, an attendant must monitor the flow of replacement fluid, and manually switch flow from one emptying bag to the next full bag before air enters the replacement line from an empty bag. In some cases the attendant must momentarily stop the flow of replacement fluid to switch flow to a new bag.

If air is inadvertently allowed to enter the infusion line from an empty bag, the machine must be stopped so that air can be removed from the flow line before it enters the patient's blood. In some cases, the entire plasmapheresis session must be scrapped and begun anew. Frequently, if a large amount of blood has been withdrawn, the patient cannot continue with a new session until sufficient time has elapsed to recuperate from the effects of the first session. Time and effort are lost while the patient is exposed to an unnecessary health risk.

The problem of replacement fluid sources going dry is compounded when multiple fluids at different rates and from separate sources are infused either sequentially or simultaneously through the single venipuncture needle. For instance, typically the reinfusion mixture contains concentrated red blood cells and sufficient anticoagulant to prevent coagulation of the red cells. At the same time, a replacement fluid, usually saline, is introduced at a rate sufficient to substitute for the plasma removed. Under certain circumstances it may be desirable to add another fluid to the mixture, such as albumin, frozen plasma, a medicament, or the like. The need exists, therefore, for a method and apparatus adapted to prevent multiple reinfusion fluid sources from going dry while monitoring the total amounts and/or relative infusion rates of the multiple reinfusion sources.

The art has long sought apparatus and equipment useful for monitoring the flow of liquid systems. It is known to monitor the flow of liquids into a fluid flow system by use of various devices. For example, in U.S. Pat. No. 4,655,742 and European patent application No. 232,263, optical detectors are used to determine when a container of fluids is full. Automatic weighing can also be effected by means of an electrical load cell that actuates an electronic device to squeeze off a tube and thereby prevent further filling of a container as disclosed in German patent No. DE 3 739 240.

Weight scales are also known for measuring the flow of blood into or out of a container. For instance, German patent No. DE 3 737 304 discloses a weighing pan connected to a pivot such that at a certain weight of blood in a bag resting on the weighing pan, a compression valve is activated to choke the flow of blood into the bag or interrupt it intermittently. In this way, unnecessary load upon the blood donor's circulatory system and heart are avoided. In addition, European Patent Application EP 87907352, filed Oct. 11, 1987, discloses a blood separation device that holds and weighs at least two separation bags that communicate with the blood bag by means of a tube. Alternatively, as disclosed in Spanish Patent No. 8 801 535, a mechanical balancing system monitoring the difference between a total instantaneous weight and an instantaneous equilibrium force can be used to regulate the flow of substitute fluid in a blood filtration device.

However, none of these devices warns the attendant when the replacement fluid source is going to run dry, provides a means for switching to an auxiliary source without temporarily stopping flow of replacement fluid into the reinfusion mixture, and/or meters the total amount of replacement fluid used from multiple sources. Thus, the need exists for new and better methods and apparatus for monitoring fluid flow systems, especially in plasmapheresis devices used for reinfusing replacement fluids to compensate for plasma removed and not reinfused.

SUMMARY OF THE INVENTION

A multiple fluid flow isolation, control and alarm system in accordance with the invention controls monitors, and meters continuous flow of fluids, usually into a fluid flow system, from a succession of containers or from multiple fluid containers. The flow control and alarm system, which is isolated from the effects of handling noise, prevents air from entering the system from an emptied container without the need for continuous visual surveillance by an attendant. The multiple fluid flow isolation, control and alarm system comprises at least one fluid container, an input fluid flow line connected at one end to the exit from the container and at the other end to a weighing bag for receiving fluids from the container(s), an output fluid flow line connected to the exit from the weighing bag, clamp means on said input fluid flow line for starting and stopping flow through said input fluid flow line, weighing means disposed for weighing the isolated fluid contents of said weighing bag., and alarm means connected to said weighing means for initiating an alarm signal when the weight of said weighing bag drops below a preselected warning level amount.

The multiple fluid flow isolation, control and alarm system can be adapted for monitoring the flow of fluids into a fluid flow system wherein it is desirable to control the exact amount of the fluids added to the flow system.

The flow control system is adapted to receive a predetermined amount of simultaneous or sequential flow from any number of containers. Preferably the containers are held by a holder so that fluid from the containers flows by gravity into the weighing bag. Replacement fluids are metered into the flow system from the weighing bag. The capacity of the weighing bag is sufficient to accommodate this function.

To implement the warning features of the system, the weighing bag is large enough to allow continuous metering therefrom of replacement fluids after a warning alarm has been initiated and while the attendant replenishes the diminishing supply of fluid therein. Thus, the operation of the plasmapheresis machine need not be halted while the weighing bag is being replenished. In the alternative, to avoid the effects of mass transport on the weighing mechanism, in one embodiment of the invention flow from the weighing bag can be halted while its contents are replenished to the desired weight.

Fluids held in the weighing bag are metered therefrom under the operation of a control means equipped to initiate an audible or visual alarm signal when the weight of fluid in the weighing bag drops below a first higher warning level and to shut down the entire plasmapheresis operation or just the flow of replacement fluid into the system when the weight of fluid in the weighing bag drops below a second lower warning level. Successive batches of one of more fluids can be metered through the weighing bag while by these means the weighing bag is prevented from becoming empty, and air is thereby prevented from entering the flow line leading therefrom.

The cumulative amount of fluids metered through the weighing bag can be determined with great accuracy by two different methods. By the first method, flow from the weighing bag is temporarily halted when successive batches of fluids are flowed into the weighing bag and the sum total of the fluids passed through the bag is found by adding together the weights of successive batches of fluid passed into the weighing bag before flow therefrom is reinitiated.

The second method is used when continuous flow from the weighing bag is desired. By this method the cumulative amount of fluid passed through the weighing bag is determined by metering continuous flow from the weighing bag through a calibrated pump. The latter method of calculating continuous fluid flow is complicated when fluids are metered through the weighing bag by means of non-invasive peristaltic pumps and the flow lines comprise disposable plastic tubings with unique flow characteristics, as are typically used in plasmapheresis. In such cases, an absolute calibration of pump performance for the replacement fluid pump can be obtained, before or at any time during the plasmapheresis operation, using the multiple fluid flow isolation, control and alarm system herein. To calibrate the fluid replacement pump, the times required at different flow rates for a given weight of fluid of known density to pass out of the weighing bag by means of the pump and plastic set is observed. The weighing bag is allowed to fill to its maximum working weight and the clamp on the input line to the weighing bag is then closed. Thus the change in weight of fluid in the weighing bag is due solely to the operation of the pump. Using this data, the weight of replacement fluid pumped from the weighing bag at a given pump flow rate setting during any period of time can then be calculated from the time of continuous operation of the pump.

In the preferred embodiment, during normal operations the weight of fluid in the weighing bag cycles between upper and lower working level limits preselected for convenience, for example between an upper limit of 200 grams and a lower working limit of 100 grams. At the start of operations, the weighing bag is filled to the upper limit by opening the clamp on the input line and allowing an influx of fluid therein. Then the clamp is closed, the fluid pump is started, and the weight of fluid in the weighing bag continuously decreases down to the lower working limit, at which point the clamp on the input line is opened and fluid again flows into the weighing bag until the upper limit is reached, at which point the clamp again closes. In this embodiment of the invention, the pump can be automatically recalibrated each time the weight of fluid in the weighing bag moves from the upper to the lower working limit. The amount of fluid pumped during the next following filling period (while the weight of fluid moves from the lower to the upper working limit) is then calculated upon the basis of the immediately preceding pump calibration. In this way, the pump can be continually recalibrated to compensate for changes in the resiliency of the tubing set caused by temperature change, and the like.

The multiple fluid flow system herein provides an automatic warning alarm when the weight of fluid in the weighing bag drops below a certain predetermined warning level selected to be below the lower working limit. The attendant is given sufficient warning before the weighing bag empties that the supply of replacement fluids in the weighing bag can be replenished, manually if necessary, without shutting down the flow of fluids through the system. If the weight of the weighing bag continues to diminish, for instance, because the supply of fluid therein has not been replenished, at a second, lower predetermined fail safe weight of fluid the automatic fail-safe feature of the system shuts down all operations or stops the flow of the replacement fluids.

The flow control and alarm system herein also provides an automatic self-checking feature to eliminate the possible hazards inherent in automatically controlled operations. This feature automatically generates an error signal when, according to the most recent pump calibration, the pump has been running long enough to reduce the weight of the weighing bag from the upper working level to below the lower working level but the actual weight of fluid in the weighing bag has not decreased accordingly.

In the preferred embodiment, the multiple fluid flow isolation, control and alarm system of the invention is adapted to continuously meter known, exact amounts of replacement fluid, into a disposable plastic flow set of the type used with a typical plasmapheresis machine. The replacement fluid, usually several aliquots of saline from pre-packaged, sterile containers, usually holding about 500 to 1000 milliliters of fluid each, is added without allowing air to enter the flow set and mix with the blood to be returned to the patient. Other fluids can also be added either mixed with the saline or separately.

In addition to the multiple fluid flow isolation, control and alarm system described in detail herein, the flow set, sometimes known as a "harness set", includes a blood separator to separate out and collect a blood component while returning to the donor or patient the balance of the blood, along with sufficient replacement fluid to compensate for the component removed. When blood withdrawal and fluid reinfusion is cyclic, a single attachment means to the patient is used, such as a single phlebotomy needle. On the other hand, when both operations proceed simultaneously, the flow set includes two means of attachment to the donor or patient, such as separate withdrawal and reinfusion phlebotomy needles.

Brief Description of the Drawings

A better understanding of the invention can be had from a consideration of the following detailed description, taken in conjunction with the accompanying drawings in which.

Detailed Description of the Preferred Embodiment

Figure 1:
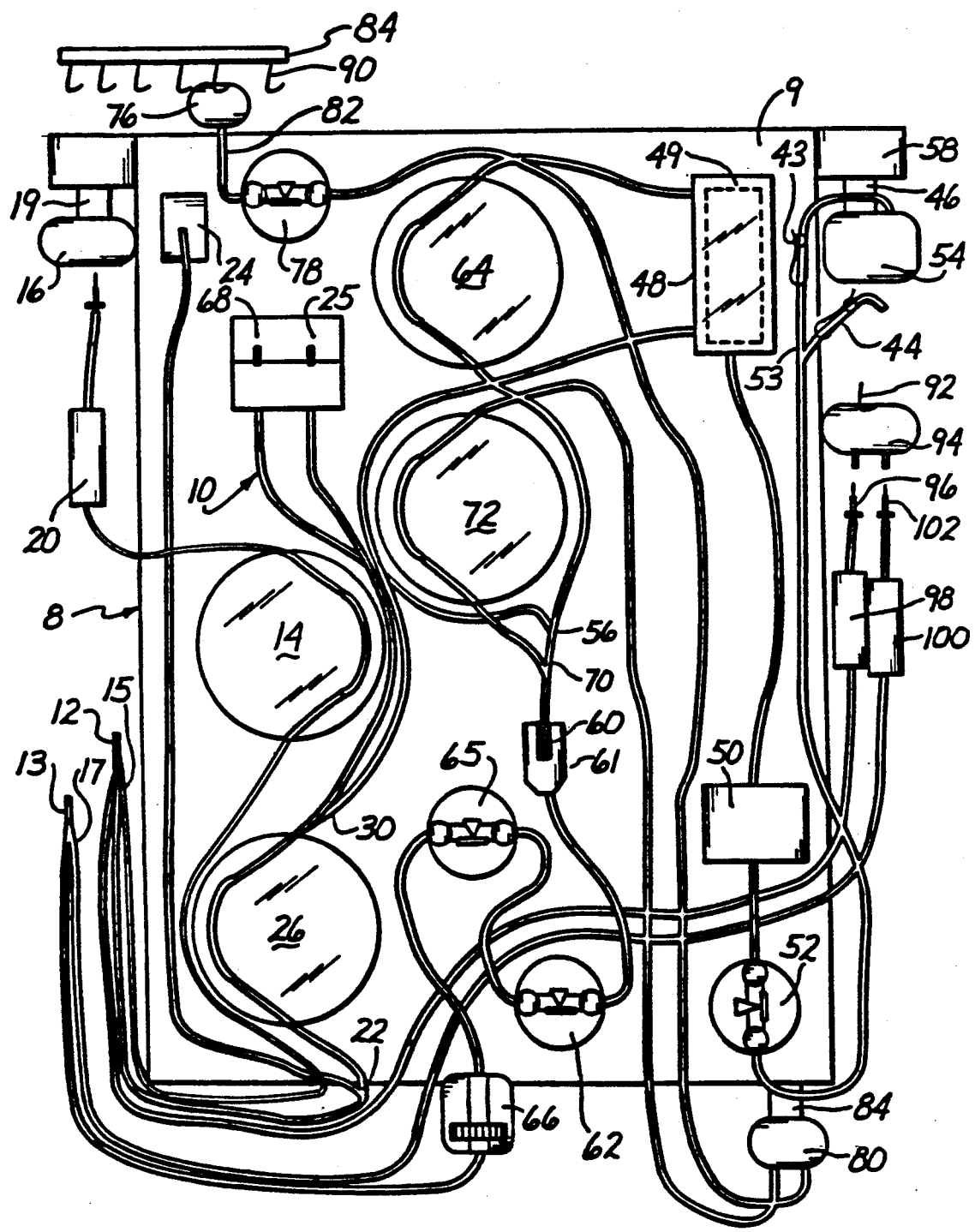
FIG. 1 is a schematic and block diagram representation of a fluid flow path for a plasmapheresis system using a multiple fluid source isolation, metering, and alarm system in accordance with the invention.
Figure 2:
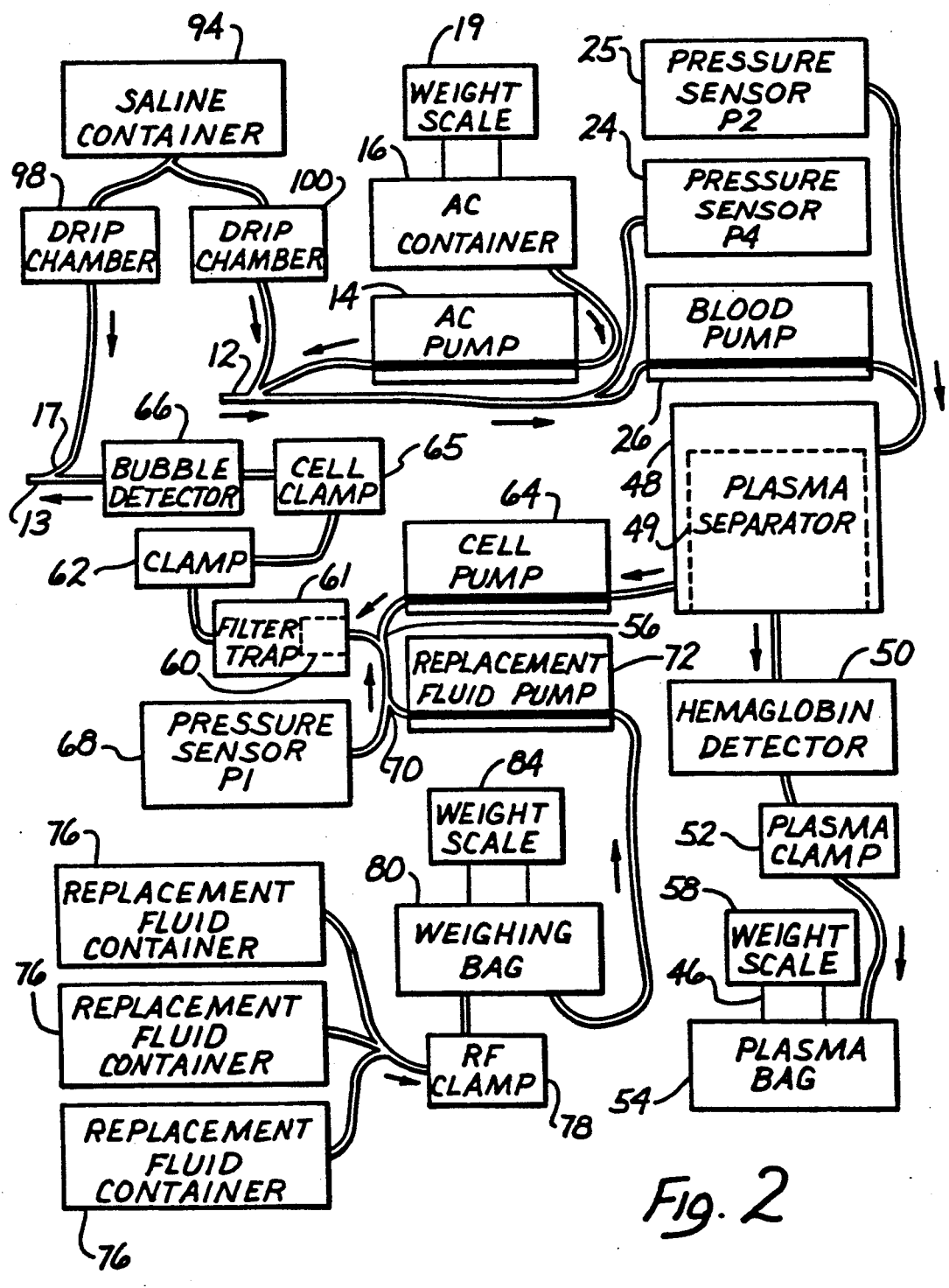
FIG. 2 is a functional block diagram representation of a plasmapheresis system incorporating a multiple fluid source isolation, metering, and alarm system in accordance with the invention.

Referring now to FIG. 1, a conventional plasmapheresis instrument is generally designated B and includes various pumps, clamps, detectors, monitoring systems, indicators, and the like, not all of which are described in the present application or necessary to an understanding of the present invention. Therefore, only those parts of the instrument which are applicable for an understanding of the present invention will be described.

Instrument 8, on its face 9, includes four peristaltic pumps which are individually driven and under the control of a computerized control system. A disposable harness set, according to the present invention, is applied to the instrument and to the donor such that blood collection, separation and infusion of packed cells with replacement fluid can be provided. Flow path 10 of the disposable harness set will now be described.

Flow path 10 provides a noninvasive, sterile plasmapheresis flow path for a dual needle plasmapheresis system utilizing a multiple fluid flow isolation, control and alarm system in accordance with the invention. Intravenous connection of flow path 10 to a subject is provided by dual bodily fluid flow channel connections such as phlebotomy needles 12 and 13 which are suitable for insertion into the veins of a living (or deceased) subject to provide bidirectional communication of blood and other fluids between the subject and flow path 10 of the plasmapheresis system.

The flow path branches immediately adjacent withdrawal needle 12 at branch point 15 with one branch extending through a noninvasive peristaltic anticoagulant pump 14 and drip chamber 20 to an anticoagulant container 16 held by holder 19. During operation, anticoagulant pump 14 operates to supply and mix a small percentage of anticoagulant with the blood as it is being extracted to prevent activation of clotting mechanisms that would cause the blood to cling to tubing sidewalls as it passes through flow path 10. By mixing the anticoagulant with the whole blood at needle 12, the two fluids become fully mixed during withdrawal and less anticoagulant is required. This desirable result helps minimize the amount of anticoagulant introduced into the blood.

The other branch of blood flow path 10 leaving withdrawal needle 12 extends to another branch point 22. Optionally, from branch point 22 one branch extends to a pressure sensor 24 coupled to sense fluid pressure on the subject side of a blood pump 26. The pressure sensor 24 includes a disposable filter coupling the sensor to a pressure sensor tube (not shown) so as to maintain a noninvaded sterile atmosphere within the flow path 10. The second branch from branch point 22 extends through the noninvasive, peristaltic blood pump 26 to branch point 30. From branch point 30 one branch leads to pressure sensor 25, which also includes a disposable filter coupling to maintain sterility. Pressure sensor 25 detects pressure across filter 49 in separator 48. Another flow path from branch point 30 extends to the bottom of plasma separator 48, which encloses filter 49.

While the exact nature of the plasma separator 48 is not material to the present invention and can be fully conventional if desired, a highly advantageous plasma separator is a centrifugal filter type of separator as illustrated in U.S. patent application Ser. No. 591,925 filed Mar. 21, 1984, entitled "Method and Apparatus for Separation of Matter from Suspension" by Donald Schoendorfer. For this type of separator the end product plasma output is coupled through a hemoglobin detector 50 and a plasma clamp 52 through branch point 53 and clamp means 43, such as a roller clamp, to a plasma container 54, which is maintained at atmospheric pressure. The plasma container 54 is suspended from a hanger means 46 of a weight scale 58, which provides feedback to the plasmapheresis system of the amount of plasma within container 54. Another open ended flow path from branch point 53 extends through clamp means 44, such as a roller clamp, for attaching an auxiliary plasma container (not shown) to flow path 10.

A cell pump 64 coupled with an outlet of plasma separator 48 controls the reinfusion flow of high hematocrit blood from plasma separator 48 through a flow path extending through branch points 56, and 70, filter 60 and flexible bubble trap 61, blood clamps 62 and 65, air detector 66, branch point 17, and reinfusion needle 13. From branch point 56 another flow path extends to pressure sensor 68. Since plasma removed from separator 48 is maintained at atmospheric pressure plus a small adjustment for vertical height differences, the difference between pressure sensors 68 and plasma container 54 provides an indication of pressure across filter 49 within plasma separator 48. This pressure indication can be useful in monitoring and controlling the operation of plasma separator 48.

Figure 3:
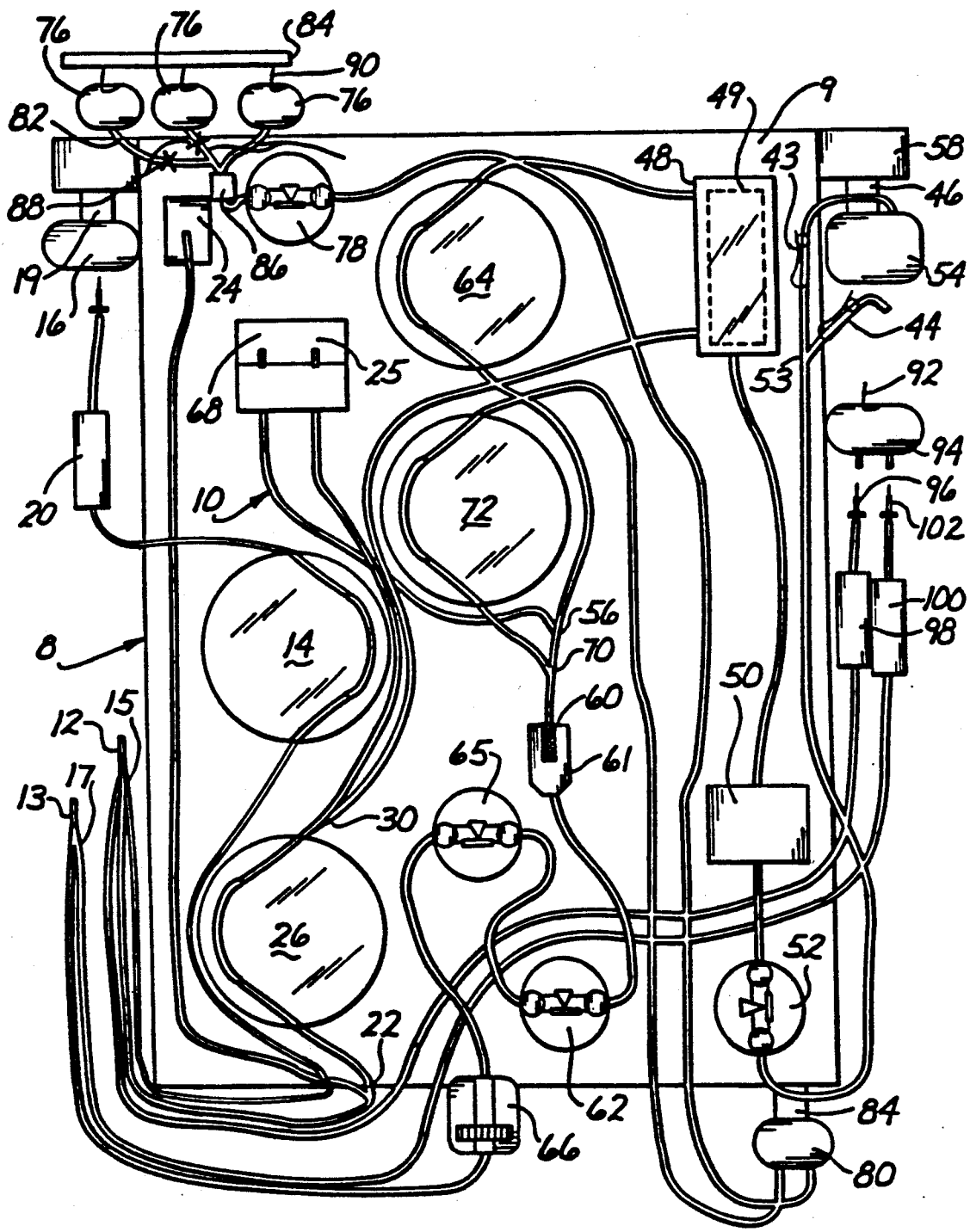
FIG. 3 is a schematic and block diagram representation of a fluid flow path for a plasmapheresis system using a multiple fluid source isolation, metering, and alarm system in accordance with the invention wherein multiple fluid sources are connected to the weighing bag.

From branch point 70, another flow path extends through replacement fluid pump 72 to replacement fluid weighing bag 80. Weighing bag 80 is suspended from scale means 84, and another flow path extends from weighing bag 80 through clamp 78 and connector 82 to one of a plurality of fluid containers 76. In an alternative embodiment, as shown in FIG. 3, from clamp 78 the flow path extends to drip chamber 86 at the exit from which it branches into a plurality of flow paths extending to a plurality of connectors 82, such as a plastic spikes, and individual fluid containers 76. A clamp means 88 is located along each reinfusion line 82 for independently controlling the flow of fluid therethrough to weighing bag 80. In drip chamber 86 fluids from any or all of containers 76 are received and mixed. Usually at least one of fluid containers 76 is filled with saline. Others of the fluid containers 76 can also be filled with supplementary bags of saline. In both embodiments shown in FIGS. 1 and 3, fluid containers 76 are suspended or supportably attached by attachment means 90 to replacement fluid holder 84.

Returning now to FIG. 1, from branch point 15 a third branch of the flow line extends through drip chamber 98 and connector 96 to saline bag 94 suspended from attachment means 92. From branch point 17 near reinfusion needle 13 a second branch of the flow path extends through drip chamber 100 and connector 102 to saline bag 94. Before and after the plasmapheresis cycle, saline from fluid container 94 can be passed through needles 12 and/or 13 to prime or cleanse the needle and thereby prevent clogging due to coagulation of blood therein. This flow path enables the separator to be primed with a small amount of saline prior to initial use and to be cleansed with saline after final use. If for any reason the plasmapheresis cycle is temporarily halted, saline can be dripped through needles 12 and 13 to keep them open until operations are reinitiated. The saline drip preferably can be initiated manually by the attendant opening control means (not shown), such as a roller clamp. Alternatively, the computerized control means can initiate the saline drip therethrough whenever the fail safe mechanism shuts down operations, as further described hereinbelow.

During normal operations the weight of fluid in the weighing bag cycles between upper and lower working level limits preselected for convenience, for example between an upper limit of 200 grams and a lower working limit of 100 grams. To initiate the cycle at the start of operations, after the system has been primed and the pump 72 has been initially calibrated, the weighing bag 80 is filled to the upper limit by opening the clamp 78 on the input line and allowing an influx of fluid therein. Then the clamp 78 is closed, pump 72 is started, and the weight of fluid in the weighing bag continuously decreases down to the lower working limit, at which point the clamp on the input line is opened and fluid again flows into the weighing bag until the upper limit is reached, at which point the clamp again closes. In this embodiment of the invention, the pump can be automatically recalibrated each time the weight of fluid in the weighing bag moves from the upper to the lower working limit. The amount of fluid pumped during the next following filling period (while the weight of fluid moves from the lower to the upper working limit) is then calculated upon the basis of the immediately preceding pump calibration. In this way, the pump can be continually recalibrated to compensate for changes in the resiliency of the tubing set caused by temperature change, and the like.

During plasmapheresis, using the apparatus and method of this invention, blood from the patient is withdrawn through needle 12, and sent through separator 48 for removal of plasma therefrom. Replacement fluids are simultaneously withdrawn from weighing bag 80 via pump 72, mixed with red cell concentrate at branch point 70 (pumped via pump 64 from the separator 48 outlet), and reinfused to the patient via needle 13. When used for plasma replacement therapy, plasma usually is considered waste and discarded., however, the plasma can also be retained and given therapeutic treatment by known means. Although one skilled in the art will appreciate that the apparatus could be modified to perform cyclic withdrawal and reinfusion functions, preferably withdrawal, separation and reinfusion proceed simultaneously. In either the cyclic or sequential modes of operation, the reinfusion mixture returned to the patient via reinfusion needle 13 comprises concentrated cells of increased hematocrit and anticoagulant recovered from the separator 48 and sufficient replacement fluid from individual replacement bag(s) 76 to replace in any proportion the amount of plasma collected in weighed plasma bag 54 as directed by the treating physician.

Attached to scale means 84 is an alarm means, not shown, for providing a visual or audible signal whenever during plasmapheresis the amount of fluid contained in weighing bag 80 drops below a preselected relatively low warning amount, preferably from about 75 to 85 grams. In addition, scale means 84 is provided with an automatic fail safe means (not shown) for shutting down the plasmapheresis operation whenever the amount of fluid in weighing bag 80 drops below a second, lower preselected fail safe amount. The difference between the warning amount and the fail safe amount is any convenient amount selected to allow the attendant sufficient time to add additional fluids to weighing bag 80 while pump 72 continues to run before it empties to the fail safe amount. The exact amount of the difference between the warning and fail safe amounts, of course, will usually differ depending upon the rate of pump 72.

The control and alarm system herein also provides an automatic self-checking feature to eliminate the possible hazards inherent in automatically controlled operations. The control means automatically generates an audible or visual error signal when pump 72 has been running with clamp means 78 closed long enough to deplete the weight of fluid in the weighing bag some preselected amount, preferably from the maximum working weight at initiation of operations, but the actual weight of fluid in the weighing bag has not dropped a corresponding amount.

In use, the harness set comprising flow path 10 is applied to face 9 of instrument 8 as illustrated in FIG. 1. Separator 48 is placed into a motor mount (not shown) and flow path 10 is threaded into the anticoagulant pump 14, blood pump 26, cell pump 64, and replacement fluid pump 72, as well as clamps 78, 65, 62, and 52. Weighing bag 80 is hung from scale 84 and plasma bag 46 is hung from scale 58. Replacement fluid bags 76 are hung from attachment means 90 and at least one of them is attached to flow path 10 using a connector 82. Saline bag 94 is hung from attachment means 92 and attached to flow path 10 via connectors 96 and 102.

In operation, various set-up and safety procedures are followed and the attachment means 12 and 13 are phlebotomy needles applied to the patient. To utilize the multiple fluid flow isolation, control and alarm system features of the invention, clamp 78 is opened and a known quantity of replacement fluid from one or more of the replacement fluid bags 76 is allowed to circulate, for example by gravity flow, into replacement fluid weighing bag 80. Clamp 78 is then closed. The amount of fluid circulated into weighing bag 80 is sufficient to allow plasmapheresis operations to proceed at least until an additional isolated aliquot or batch of replacement fluids can be circulated into weighing bag 80 by repeating the above steps, usually at least 100 grams or more. Preferably, however, no more than between about 100 and 200 grams at a time are circulated into weighing bag 80 to facilitate switching from one replacement fluid type to another without emptying weighing bag 80. Optionally several of bags 76 can contain the same type of fluid and connector 82 can be moved from one to the next to empty several of bags 76 into weighing bag 80 in a single batch.

Plasmapheresis is initiated by opening clamps 52, 62 and 65 and starting pumps 26, 14, 64 and 72. Blood from the patient mixed with anticoagulant in proportions controlled by the relative rates of pumps 14 and 26 flows to separator 48 wherein plasma is separated and circulated to plasma bag 54. Simultaneously, concentrated cells recovered from separator 48 are circulated by pump 64 to branch point 70 where they are joined by a flow of replacement fluid from weighing bag 80 at a rate controlled by pump 72. The replacement fluid is usually delivered in some predetermined ratio to the amount of plasma being removed to plasma bag 54. When the amount of fluid in weighing bag 80 drops below the preselected warning amount, the alarm attached to weighing bag 80 is triggered to produce either an audible or visible alarm.

The alarm means and fail safe means attached to weighing means 84 can utilize known methods of triggering mechanical alarm. Preferably, however, the alarm and fail safe means are incorporated within a programmed digital processor that controls the operation of the plasmapheresis machine using known principles.

The warning alarm alerts the attendant that replacement fluid weighing bag 80 is approaching empty. In response to the warning alarm, the attendant can replenish the replacement fluid in bag 80 before it runs dry by either of two methods. By the first, less preferred method the attendant stops either pump 72 or all of pumps 26, 14, 64 and 72, checks to see that one of the replacement fluid bag(s) 76 contains at least an aliquot of fluid, and opens the clamp 78 on the bag 76 to allow fluids therefrom to empty into weighing bag 80 until the weight of replacement fluid in weighing bag 80 is increased above the warning level and the pump or pumps are all restarted. By the second, more preferred method the pumps are not stopped and the contents of bag 80 continue to empty while the auxiliary fluid replacement bags 76 are positioned by the attendant and emptied as described above into bag 80.

If the amount of replacement fluid in weighing bag 80 is not replenished before the weight of fluid therein drops to the fail safe amount, the automatic fail safe means associated with weighing means 84 shuts down operations by stopping either pump 72 alone or pumps 14, 26, 64, and 72 and closing clamps 52, 62 and 64, and generates a fail safe alarm message for the attendant. Once the control means has shut down operations, the control means stops or removes the fail safe alarm and operations of the system can be reinitiated by starting the pump or pumps and opening clamps 72, 62, and 64 when the replacement fluids in weighing bag 80 have been replenished to some predetermined reinitiation amount selected to be intermediate between the warning amount and the fail safe amount, preferably at least 30 grams above the fail safe amount. When the weight of fluid in the weighing bag rises above the reinitiation amount, system operations are reinitiated either manually in response to cessation or removal of the fail safe alarm, or automatically by the control means.

This fail safe feature prevents weighing bag 80 from completely emptying so that air never enters flow path 10 from bags 76 or from weighing bag 80. Therefore, once the amount of fluid in bag 80 has been replenished, the system operation can be continued and does not have to be scrapped.

The flow characteristics of each plastic set are necessarily unique due to slight variations in internal diameter, and the cumulative effect of connectors and branch points upon flow dynamics. Thus the performance of pump 72 is different with each flow set used and can change during the course of the procedure. Despite these differences, replacement fluid pump 72 can readily be calibrated to take into account the individual flow characteristics of flow path 10 using the multiple fluid flow isolation, control and alarm system herein. To accomplish this, either before or during plasmapheresis, with clamp means 78 closed, the time required to pump any known amount of fluid from weighing bag 80 through the associated portions of flow path 10 is noted and the rate of delivery of pump 72 is readily derived by known means.

Absolute calibration of pump 72 by this method provides the advantage that the total amount of replacement fluid delivered to the patient from the replacement fluid bags 76 can be determined with great accuracy whether the replacement fluid consists essentially of a single fluid, such as saline, or whether it comprises a mixture of saline and other therapeutic fluids, such as liquid antibiotics and the like. Thus, the physician's instructions regarding the needs of the patient can be accomplished with great accuracy despite the effect of the individual flow characteristics of the harness set upon the performance of pump 72. Preferably the system is recalibrated during each weighing bag cycle during the time the weight in weighing bag 80 moves from the upper working limit to the lower working limit and the pump calibration thus obtained is used to compute the amount of fluid delivered by pump 72 during the next following fill cycle, while the weight in the weighing bag 80 moves between the lower working limit and the upper working limit.

While the invention has been described in connection with what is presently considered to be the most practical and preferred embodiments, it is to be understood that the invention is not to be limited to the disclosed embodiments, but on the contrary, is intended to cover various modification and equivalent arrangements including within the spirit and scope of the appended claims.

What we claim is:

1. An apparatus for monitoring the weight of fluid flow from containers, said apparatus comprising:
    at least one replacement fluid container of limited capacity;
    an input fluid flow line connected at one end to the exit from the container and to a weighing bag at the other end;
    means to preconnect a plurality of replacement fluid containers to said input fluid flow line;
    an output fluid flow line connected to the exit from the weighing bag;
    clamp means on said input fluid flow line for starting and stopping flow through said input fluid flow line;
    weighing means disposed for weighing the fluid contents of said weighing bag; and
    alarm means connected to said weighing means for initiating an alarm signal when the weight of said weighing bag drops below a preselected warning amount.

2. The apparatus of claim 1 wherein a plurality of fluid containers is connected to the fluid flow line.

3. The apparatus of claim 1 further comprising alarm means connected to said weighing means for shutting down flow from said weighing bag when the weight of fluid in the bag drops below a preselected fail safe amount, the warning amount being higher than the fail safe amount.

4. The apparatus of claim 3 further comprising an automatic control system connected to said weighing means for controlling flow into and out of the weighing bag.

5. The apparatus of claim 4 wherein the automatic control system is further connected to the clamp means and wherein the control system automatically opens the clamp means when the weight of fluid in the weighing bag reaches a lower working limit amount and automatically closes the clamp means when the weight of fluid in the weighing bag reaches an upper working limit amount.

6. The apparatus of claim 5 further comprising a fluid pump connected to said output fluid flow line to pump the fluid from said weighing bag, wherein said control system is adapted to automatically recalibrate said fluid pump when the weight of the fluid in said weighing bag drops from the upper working limit to the lower working limit.

7. The apparatus of claim 1 wherein a drip chamber is located on said input fluid flow line for removing bubbles from fluids introduced into the fluid flow system.

8. The apparatus of claim 1 wherein said apparatus further comprises fluid holder means for holding a plurality of fluid containers of limited capacity so that at least one of said containers is connected to said weighing bag via said input flow line and so that fluid from the containers flows into the weighing bag.

9. The apparatus of claim 8 wherein a plurality of containers of limited capacity are held by said fluid holder means and are connected to said weighing bag via said input flow line so that fluid from the containers flows by gravity into the weighing bag.

10. The apparatus of claim 1 wherein the output fluid flow line connects at the distal end to the exit from the weighing bag and at the proximal end to a fluid flow system.

11. An apparatus for monitoring the amount of fluid flow from replacement fluid containers into a disposable flow line for use in plasmapheresis, said apparatus comprising:
    at least one replacement fluid container of limited capacity;
    a replacement fluid weighing bag;
    an input fluid flow line connected at one end to the exit from the container and at the other end to a replacement fluid weighing bag;
    an output fluid flow line connected at one end to the exit from the weighing bag and at the other end to a disposable plasmapheresis fluid flow system for withdrawing whole blood from a subject, separating out and collecting a first blood fraction therefrom and for reinfusing into the subject a mixture of replacement fluid and the remaining blood fraction;
    weighing means disposed for weighing the fluid contents of the weighing bag;
    alarm means connected to the weighing means for initiating an alarm signal when the weight of fluid in the weighing bag drops below a preselected warning amount; and
    control means connected to the weighing means for controlling flow of replacement fluid into and out of the weighing bag.

12. The apparatus of claim 11 further including clamp means on said input fluid flow line for starting and stopping flow through said fluid flow line and wherein the control means operates automatically to open the clamp when the weight of fluid in the weighing bag reaches a lower working limit amount and to close the clamp when the weight of fluid in the weighing bag reaches an upper working limit amount.

13. The apparatus of claim 12 wherein the control means automatically shuts down flow from the weighing bag when the weight of fluid in the weighing bag drops below a preselected fail safe amount lower than the warning amount.

14. The apparatus of claim 12 wherein a plurality of fluid containers is connected to the input fluid flow line.

15. The apparatus of claim 12 wherein a drip chamber is located on the input fluid flow line for removing bubbles from fluids introduced into the fluid flow system.

16. The apparatus of claim 12 wherein the apparatus further comprises fluid holder means for holding a plurality of fluid containers so that at least one of the containers is connected to the weighing bag via the input flow line.

17. The apparatus of claim 15 wherein a plurality of replacement fluid containers are held by the fluid holder means and are connected to the weighing bag via the input flow line.

18. The apparatus of claim 17 wherein each replacement fluid container is attached to the entrance into a drip trap and the exit from the drip trap is attached to the input fluid flow line.

19. The apparatus of claim 12 further comprising a fluid pump connected to said output fluid flow line to pump the fluid from said weighing bag, wherein said control means is adapted to automatically recalibrate said fluid pump when the weight of the fluid in said weighing bag drops from the upper working limit to the lower working limit.

20. A plasma exchange system for separating blood received from a subject into constituents and infusing the subject with a first blood constituent and a replacement fluid, comprising:
a separator for separating first and second blood constituents from whole blood;
an attachment means for continuously withdrawing whole blood from a subject and supplying the blood to the separator;
means for introducing anticoagulant to the whole blood withdrawn from the subject;
an attachment means for continuously reinfusing the subject with the first blood constituent and a replacement fluid;
a fluid replacement supply source;
flow means including the withdrawal attachment means for flowing the whole blood and the anticoagulant to the separator and means including the reinfusion attachment means for receiving the first blood constituent from the separator and the replacement fluid from the replacement fluid source and for flowing the first blood constituent and the replacement fluid to the subject;
control means in communication with the fluid replacement supply source for monitoring the amount of replacement fluid flowed to the subject from the fluid replacement supply source and for initiating a warning alarm when the supply source approaches empty; and wherein the control means comprises a weighing bag and attached weighing means interposed between the fluid replacement supply source and the flow means for sequentially receiving and weighing isolated amounts of replacement fluid passing from the supply source to the flow means.

21. The system of claim 20 wherein the control means comprises a weighing bag and attached weighing means interposed between the fluid replacement supply source and the flow means for sequentially receiving and monitoring the total weight of replacement fluid passed from the supply source to the flow means and further comprises a clamp means attached to the flow means and wherein the control means opens the clamp means when the weight of fluid in the weighing bag drops to a lower working limit amount and closes the clamp means when the weight of fluid in the weighing bag rises to the an working limit amount.

22. The system of claim 21 further comprising a replacement fluid holder means capable of holding a plurality of replacement fluid supply sources, with means for connecting at least one fluid source in fluid communication with the weighing bag.

23. The apparatus of claim 21 wherein said flow means comprises a fluid pump connected to said reinfusement attachment means to pump the fluid from said weighing bag, wherein said control means is adapted to automatically recalibrate said fluid pump when the weight of the fluid in said weighing bag drops from the upper working limit to the lower working limit.

24. The system of claim 21 wherein the control means is adapted to initiate the warning alarm when weight of fluid in the weighing bag drops below a warning level amount wherein the warning level amount is below the lower working limit amount.

25. The system of claim 24 wherein the control means is further adapted to shut down flow throughout the flow means when weight of fluid in the weighing bag drops below a fail safe amount wherein the fail safe amount is below the warning level amount.

26. The system of claim 24 wherein the control means is adapted to reinitiate flow manually throughout the flow means after a fail safe shut down when the fluid in the weighing bag rises above a preselected reinitiation amount and wherein the reinitiation amount is at least 30 grams above the fail safe amount.

27. The system of claim 26 wherein the control means is adapted to control a pump for removing fluid from the weighing bag and a means for opening and closing fluid communication between the supply source and the weighing bag and wherein the control means is further adapted to generate an error signal when the pump has operated for a period of time and at a rate sufficient to remove a preselected amount of fluid from the weighing bag, but the weight of fluid in the weighing bag has not dropped a corresponding amount.

28. The system of claim 27 wherein the control means is adapted to generate an error signal when the pump has operated at a rate sufficient to remove 150 grams of fluid from the weighing bag.

29. The system of claim 25 wherein the control means is adapted to shut down flow throughout the flow means when weight of fluid in the weighing bag drops below 15 grams of fluid.

30. The system of claim 24 wherein the control means is adapted to reinitiate flow throughout the flow means after a fail safe shut down when the fluid in the weighing bag rises above a preselected reinitiation amount selected to be intermediate between the warning amount and the fail safe amount.

31. The system of claim 24 wherein the control means is adapted to initiate the warning alarm when the weight of fluid in the weighing bag is from 75 to 85 grams of fluid.

32. A method of monitoring fluid flow from one or more containers having a limited fluid source into a fluid flow system so as to prevent air from an empty container entering the flow system, said method comprising:

(1) flowing a first isolated amount of fluid from at least one of said fluid sources into a weighing bag;
(2) weighing the fluid in the weighing bag;
(3) controlling the flow of fluid from the fluid source such that fluid is flowed into the weighing bag when the weight of fluid in the bag has dropped below a preselected lower working limit and fluid flow into the weighing bag is stopped when the weight of fluid in the weighing bag rises above a preselected upper working limit; and
(4) initiating flow from the weighing bag into the flow system until the weight of fluid falls below the lower working limit.

33. The method of claim 32 further including the step of automatically controlling the flow of fluid from the fluid source to the weighing bag so that the weighing bag is replenished by fluid from the fluid source without stopping operation of the fluid flow system.

34. The method of claim 32 further including the steps of repeating steps (1), (2), (3) and (4) a plurality of times.

35. The method of claim 34 wherein each isolated amount of fluid comprises from 100 to 200 grams.

36. The method of claim 34 wherein the step of initiating flow from the weighing bag into the flow system includes the steps of pumping fluid from said weighing bag and automatically recalibrating the pump when the fluid in said weighing bag drops from the upper working limit to the lower working limit.

37. The method of claim 32 wherein the isolated amount of fluid comprises from 100 to 800 grams.

38. The method of claim 32 further including the following steps:
(5) triggering a warning alarm when the weight of fluid in the weighing bag drops below a warning amount which is below the lower working limit amount; and
(6) initiating flow, in response to the warning alarm, into the weighing bag of an additional isolated amount of fluid from at least one fluid source so that the weight of fluid in the weighing bag is raised above the warning amount.

39. The method of claim 38 further including the step of adding together the weights of the isolated amounts of fluid flowed into the weighing bag to compute the total amount of the fluid flowed therefrom into the flow system.

40. The method of claim 32 further including the following steps:
(7) triggering a fail safe alarm when the weight of the fluid in the weighing bag drops below a fail safe amount which is lower than the warning amount;
(8) shutting down flow from the weighing bag in response to the fail safe alarm;
(9) initiating sufficient flow of an additional isolated amount of fluid from at least one fluid source into the weighing bag to raise the weight of fluid therein above the warning amount; and
(10) reinitiating flow from the weighing bag into the flow system.

41. The method of claim 40 wherein each isolated amount of replacement fluid comprises from 100 to 200 grams of fluid and including the step of stopping fluid flow throughout the flow means in response to the fail safe alarm.

42. The method of claim 41 wherein the warning amount is from 65 to 85 grams.

43. The method of claim 42 wherein the fail safe amount is about 15 grams or below and including the step of automatically reinitiating fluid flow when the weight of fluid in the weighing bag rises above the warning amount.

44. A method of monitoring fluid flow from replacement fluid sources into a disposable non-invasive fluid path used for plasmapheresis so as to prevent air from an empty replacement fluid source entering the flow path, said method comprising:
(1) flowing a first isolated amount of fluid from at least one of said replacement fluid sources into a weighing bag;
(2) weighing the weighing bag;
(3) isolating the weighing bag from flow disturbances during weighing;
(4) continuously flowing fluid from the weighing bag into the flow path while maintaining the amount of fluid in the weighing bag between upper and lower working limits by replenishing the weighing bag from the fluid source fill.

45. The method of claim 44 wherein due to insufficient fluid source the amount of fluid in the weighing bag drops below the lower working limit further including the steps of:
(5) generating a warning alarm;
(6) initiating flow into the weighing bag in response to the warning alarm of an additional isolated amount of fluid from at least one additional replacement fluid source so that the weight of fluid in the weighing bag remains above the lower working limit amount.

46. The method of claim 45 further including the step of ensuring that the flow out of the weighing bag continues uninterrupted while step (5) is performed.

47. The method of claim 45 further including the step of temporarily interrupting flow out of the weighing bag while step (5) is performed.

48. The method of claim 44 further including the steps of:
(5) triggering a warning alarm when the weight of fluid in the weighing bag drops below a warning amount which is below the lower working limit amount;
(6) shutting down flow from the weighing bag in response to the warning alarm;
(7) initiating sufficient flow of an additional isolated amount of fluid from at least one additional replacement fluid source into the weighing bag to raise the weight of fluid therein above the warning amount; and
(8) reinitiating flow from said weighing bag into said flow path.

49. The method of claim 48 further including the step of automatically reinitiating flow from the weighing bag into the flow system when the weight of fluid in the weighing bag rises to a preselected reinitiation amount after fail safe shut down.

50. The method of claim 48 further including the step of adding together the weights of each isolated amount of fluid flowed into the weighing bag to compute the total amount of fluid flowed therefrom into the flow path.

51. The method of claim 44 further including the step of adding together the weights of each isolated amount of fluid flowed into the weighing bag to compute the total amount of fluid flowed therefrom into the flow path.

52. The method of claim 44 wherein each isolated amount of replacement fluid comprises from 100 to 200 grams of fluid.

53. The method of claim 44 wherein said step of continuously flowing fluid from the weighing bag into the flow path includes the steps of pumping fluid from said weighing bag and automatically recalibrating the pump when the fluid in said weighing bag drops from the upper working limit to the lower working limit.

* * * * *